United States Patent [19]

Milijasevic

[11] Patent Number: 5,509,901
[45] Date of Patent: Apr. 23, 1996

[54] CONTROLLED PRESSURE FLUID DELIVERY DEVICE

[76] Inventor: Zoran Milijasevic, P.O. Box 1678, Chatswood, NSW 2067, Australia

[21] Appl. No.: 30,266
[22] PCT Filed: Oct. 4, 1991
[86] PCT No.: PCT/AU91/00460
    § 371 Date: Jun. 2, 1993
    § 102(e) Date: Jun. 2, 1993
[87] PCT Pub. No.: WO92/05830
    PCT Pub. Date: Apr. 16, 1992

[30] Foreign Application Priority Data

Oct. 5, 1990 [AU] Australia .................. PK 2661

[51] Int. Cl.⁶ .................................................. A61M 1/00
[52] U.S. Cl. ........................... 604/153; 604/151; 222/96; 222/105
[58] Field of Search ..................... 604/131, 151, 604/153; 220/92, 95, 96, 105

[56] References Cited

U.S. PATENT DOCUMENTS 2,761,445  9/1956  Cherkin .......................... 604/153
3,151,616  10/1964 Selfon ............................ 604/131
5,074,756  12/1991 Davis ............................. 604/153
5,131,816  7/1992  Brown et al. .................... 604/153

FOREIGN PATENT DOCUMENTS 111842   6/1984  European Pat. Off. .......... 604/131
3911587  10/1990 Germany.

Primary Examiner—John G. Weiss
Attorney, Agent, or Firm—Richard C. Litman

[57] ABSTRACT

A constant pressure device for use with administration sets for infusing liquids into patients. The device includes a housing adapted to receive a container for holding and discharging liquid into the body of a patient. The constant pressure can be pre-set to a desired pressure according to the requirements of a particular circumstance. The device maintains constant pressure independent of gravity, relative pressure head height, or fluid viscosity. The device has a housing in which a collapsible container is inserted. The constant pressure device has a drive which exerts a predetermined pressure on the container thereby dispensing a predetermined amount of liquid. The device also has an energy storing mechanism located within the housing which is linked to a gearing assembly to control the drive. The device has a pressure-responsive mechanism to deactivate the drive when the pressure becomes too great.

18 Claims, 9 Drawing Sheets

CONTROLLED PRESSURE FLUID DELIVERY DEVICE

BACKGROUND OF THE INVENTION

The present invention relates to a constant pressure device for use in particular though not exclusively with administration sets which are used for infusing liquids into patients.

SUMMARY OF THE INVENTION

Infusing fluids into the human body is done for a variety of medical reasons and there have been a number of apparatuses which have been developed and employed for this purpose.

It is presently well known to provide for liquid infusion into a living body by providing a container acting as a reservoir for holding liquid to be infused and which is connected to the body via a conduit in which the pressure supplying the fluid is created by the gravitational pressure head.

The problem is gravity systems is that the relative height or differential height can be easily and inadvertently changed by the patient (sitting up/walking around or the level of fluid in bag dropping) and it is this change in differential height that is the substantive cause for loss of accuracy requiring manual intervention.

In these systems there are two main factors controlling the actual infusion rate of liquid to be infused into a patient. One is the relative height that the liquid reservoir or container is held relative to the discharge outlet of the fluid and the second factor is the degree of venous back pressure which is experienced as the liquid enters the patient. These factors are significant where infusion tube geometry, fluid viscosity and system resistance are constant.

For medical reasons, it is necessary and desirable on many occasions to keep the flow rate of the liquid within selected limits and this becomes either very difficult or impossible with the prior art device described above.

In the past it has therefore been a difficult matter to provide under the assistance of gravity fluid for infusion into a body at a constant flow rate and to ensure that a selected quantity of the fluid is infused into the body at any given time. The applicant has a co-pending application for a flow controller which is a device for insertion into a fluid supply line in an administration set and which is designed to provide a constant flow rate independent of the factors which may prevent a constant flow rate occurring when infusing fluids into the human body.

SUMMARY OF THE INVENTION

The present invention may be used as an adjunct to an administration set having the applicants flow controller or indeed it can be used with any type of administration set or any type of flow control device where a constant flow of infusing fluid is required.

The present invention provides a constant pressure device which is adapted to receive a container or reservoir for holding and discharging at a predetermined constant pressure a fluid for infusion into the body of a patient. The constant pressure delivery is maintained by the device independent of gravity or relative pressure head height and independent of fluid viscosity. The constant pressure device is a mechanical device which can be pre-set to a desired pressure according to the requirements of the infusion in any particular circumstance.

In broad terms the device has a receptacle in which the reservoir or container which is preferably collapsible holding the fluid is inserted. The mechanics of the constant pressure device applies a predetermined and constant pressure to the fluid irrespective of whether the container in which the fluid lies is full or nearly empty and irrespective of its attitude.

In one broad form the present invention comprises a constant pressure device comprising essentially a housing, an energy storage means, a pressure exerting surface linked either directly or indirectly to said storage means, a means for presetting the degree of pressure applied by said pressure means.

In another broad form the present invention comprises; a device for the constant pressure delivery of a fluid from a fluid reservoir for infusion into the body of a patient, said device comprising:

a housing having associated therewith a movable casing between which housing and said casing said reservoir is disposed in a recess so formed, energy storage means located within said housing which is linked to a gearing assembly to effect gearing control of drive produced from said energy storage means, means to exert pressure on said reservoir via said casing, and a pressure responsive braking assembly, wherein when fluid is to be delivered by said device, energy is induced into said energy storage means whereupon on release of said energy, pressure is exerted on said reservoir by said pressure exerting means, said drive being deactuated by said pressure responsive braking assembly and when the pressure generated exceeds a predetermined maximum threshold.

In its broadest form the present invention comprises a device for the controlled pressurised delivery of a fluid from a fluid reservoir such that it can be administered into the body of a patient at a predetermined pressure, said device comprising:

a housing having associated therewith a casing between which housing and said casing said reservoir is disposed in a recess so formed, energy storage means located within said housing which is linked to a gearing assembly to effect control of drive produced from said energy storage means, means to exert pressure on said reservoir acting in cooperation with said casing, and and pressure responsive drive deactuation means; wherein, when fluid is to be delivered by said device, release of said energy stored or induced into said energy storage means causes pressure to be exerted on said reservoir by said pressure exerting means said drive being deactuated by said pressure responsive drive deactuation means when the pressure generated exceeds a predetermined maximum operating threshold.

According to one embodiment the device delivers a constant fluid pressure so that the delivery of the fluid is gravity independent.

The device casing is operably linked to a mechanical input device which induces energy into the energy storage means and also induces movement in the casing in order to exert a pressure on the fluid reservoir.

Furthermore, the stored energy which is indirectly linked to the pressure inducing surface formed by the articulating casing is transmitted by means of a system which draws the articulating casing back to a position of equilibrium at which time the energy provided by the energy storage is momentarily isolated.

One advantage of the above described embodiment of the present invention is that it becomes unnecessary for continual manual intervention by medical staff to compensate as in the case of the prior art devices, for changes in flow rate which are necessitated where a constant flow is required.

The prior art devices which rely on gravity require constant monitoring whereas the present invention and its various embodiments do not.

According to an alternative embodiment the constant pressure device comprises a housing having disposed therein a recess for receiving a fluid reservoir, a pressure plate which is activated by energy from a drive system activated by an energy storage means to drive the plate against the reservoir to discharge fluid therefrom at a constant pressure.

The constant pressure device can be used in any attitude and at any height or position relative to the infusing inlet into the patient. Furthermore, the constant flow device can be carried by a patient being infused and it will not be affected by any movement of the patient irrespective of whether the patient is lying down or walking causing loss of pressure head.

The present invention will now be described in more detail and according to preferred embodiments of the invention and with reference to the accompanying illustrations wherein:

DESCRIPTION OF THE PREFERRED EMBODIMENTS

Figure 1:
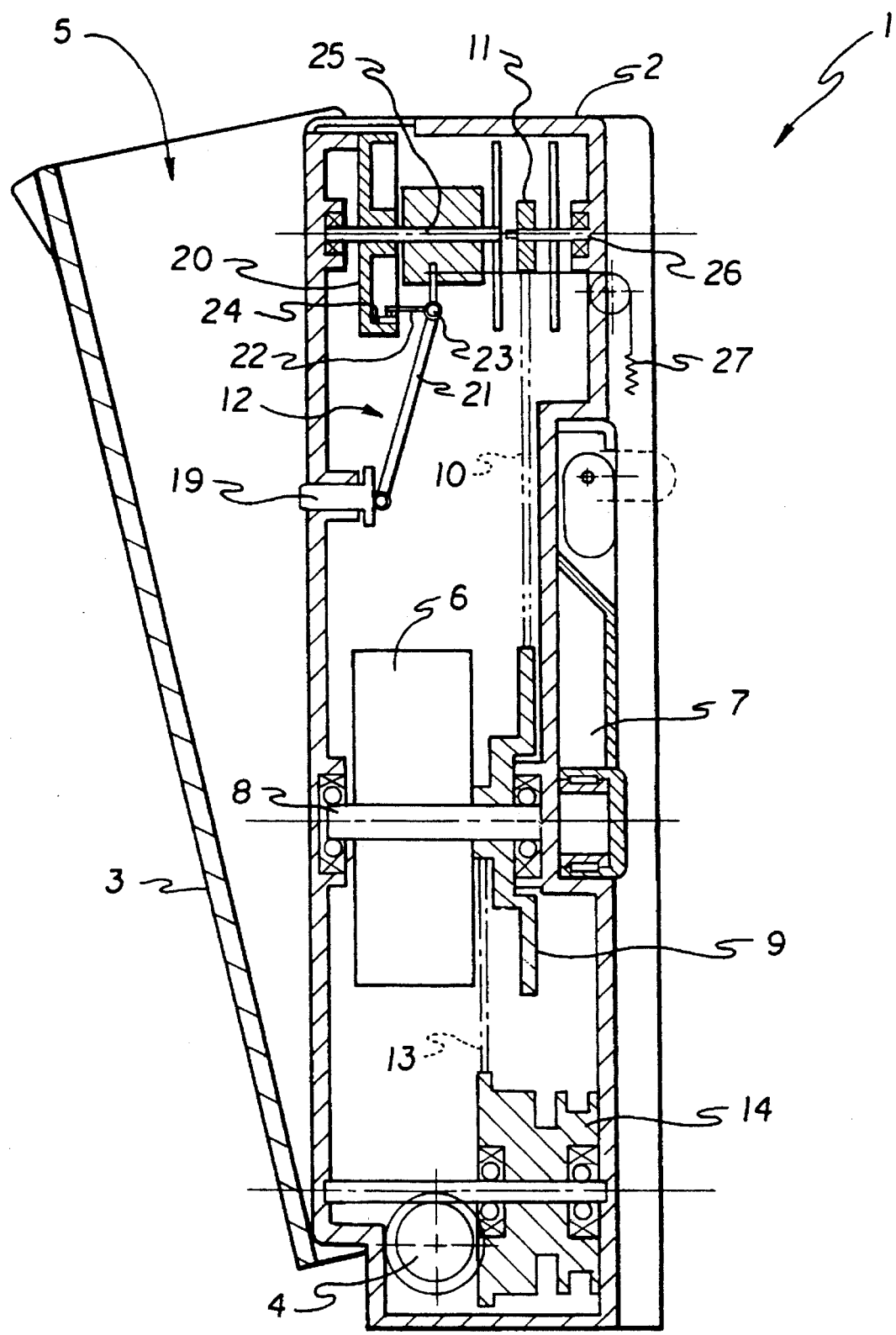
FIG. 1 shows a cross-sectional elevational view of the constant pressure device according to a preferred embodiment.

Referring to FIG. 1 there is shown a constant pressure device 1 comprising essentially a housing 2 which has attached thereto a pivoting door 3 which is attached by means of a door pivot 4 to the housing 2. The housing 2 houses the operational mechanisms which enable the door 3 to exert pressure on a fluid contained in a fluid reservoir which is in turn inserted into the receptacle 5, which is made available by the opening of the door 3. The constant pressure device relies for its energy primarily on spring energy from spring 6 which is tensioned by handle 7, which is located on the back of the housing 2.

When the device is to be used, the handle 7 is wound in order to introduce spring tension into the spring 6. The spring energy which is introduced by handle 7 is transmitted from the spring via a shaft 8 to pulley 9. Pulley 9 has around it a toothed belt 10 linked to pulley 11. Pulley 11 is associated with the braking apparatus 12 to be described below.

Pulley 9 also has attached thereto a further toothed belt 13 which transmits rotational energy to the differential pulley 14. The differential pulley 14 is in turn linked with another pulley system which is linked to articulating door 3 and which provides the linkage between the door 3 and the energy spring 6.

Figure 2:
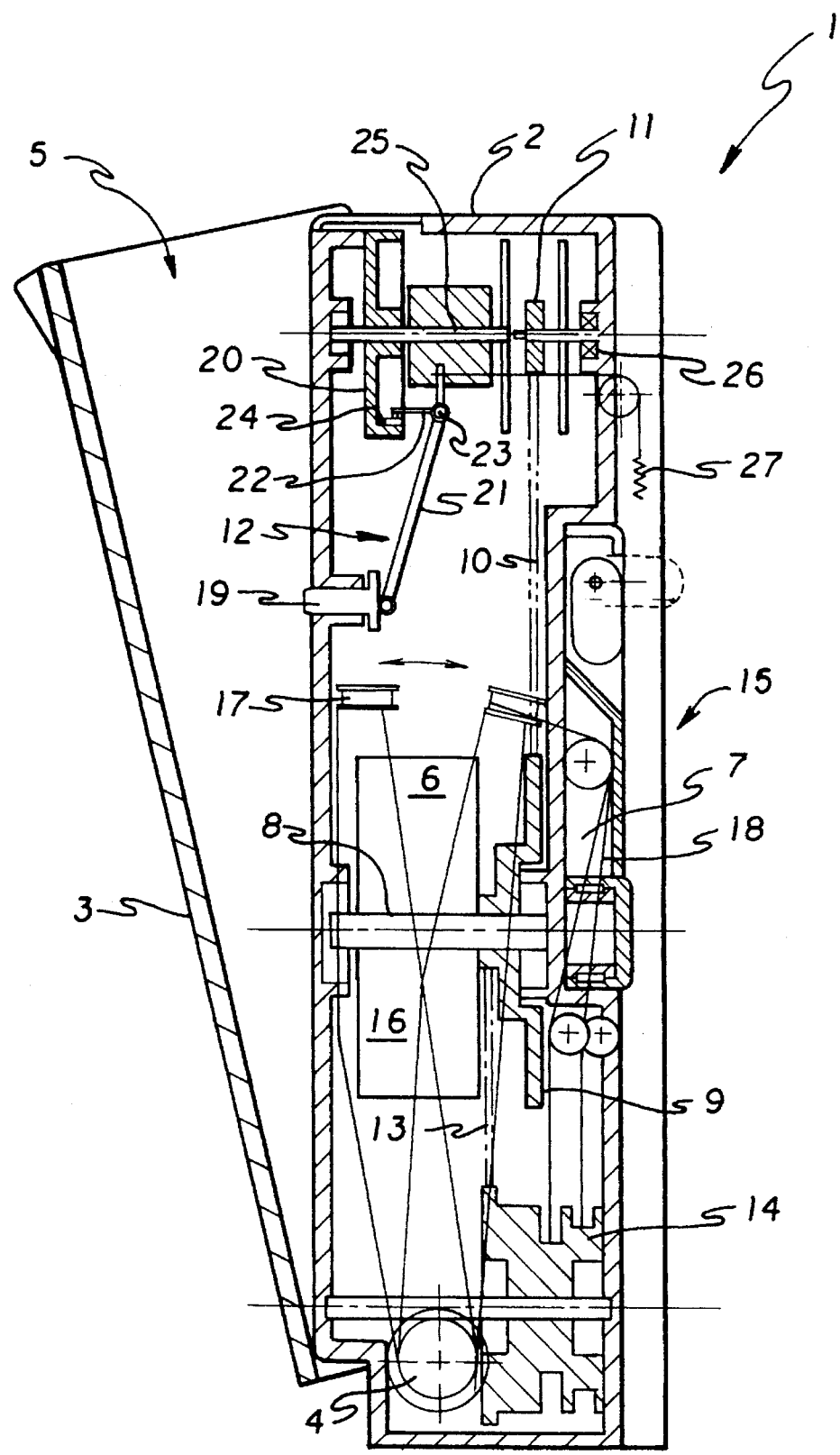
FIG. 2 shows the preferred embodiment of FIG. 1, however this time the flow controller is shown with operational pulley systems superimposed which assist in the maintenance of constant pressure on the fluid to be infused.

Referring to FIG. 2 there is shown the constant pressure device shown in FIG. 1 however, this time the device is shown with a pulley system 15 which is engaged with the differential pulley 14 and also with the articulating door 3 via an articulating support arm 16. FIG. 2 shows the articulating support arm as it is configured in both the closed and opened position of door 3. Preferably the articulating support arm 16 has a range of travel between 0 and 13 degrees however, this range of travel is not to be construed as limiting as it is conceivable that the same operational characteristic of the support arm could be achieved within a greater or smaller arc of travel.

At the top of the support arm 16 is a pulley 17 which moves when the door 3 is pulled away from the housing 2 of the constant pressure device 1. The pulley 17 has associated therewith a belt 18 which travels about differential pulley 14 in order to enable transmission of the energy from the spring 16 to the door 3. In use, when the constant pressure device is required to deliver the constant pressure, a fluid reservoir is inserted into the receptacle 5 following the pulling open of the door 3. This creates the receptacle 5 into which the reservoir sits. Prior to doing this the user must fully wind the handle 7 in order to induce potential energy into the spring 6. If the handle 7 is insufficiently wound the door 3 will not open sufficiently such that the receptacle will not be able to receive a full reservoir. When this is completed a spike of the giving set with which the constant pressure device is intended for use, is inserted into the container containing the fluid. When the container is in the recess 5, door 3 is closed against the fluid container in order to exert pressure on the fluid. At this time the pressure unit is turned on and at the same time the pressure alarm, which is linked to a microprocessor and signals a reduced power condition or a pressure switch failure condition, may be tested.

While the unit is in the upright position, the fluid supply line may be primed by holding the free end of the administration set until all air is expelled and fluid comes through. Once this priming has taken place, the fluid supply line is now ready for connection to the catheter and consequently to the patient. The stored energy from the spring 6 is transmitted via tooth belt 13 to the differential pulley 14. The displacement of the pulley arrangement 15 transfers energy from the energy spring 6 and draws the door freely towards the housing 2 as the fluid empties from the fluid container (not shown) which is inserted in recess 5. If, during the constant pressure delivery the pressure exceeds a pre-determined maximum value, the fluid container exerts pressure on pressure sensing piston 19. As the braking assembly 12 is indirectly linked to the energy source via toothed belt 10, pressure exerted on the pressure sensor piston 19 results in a braking action against spinning indicator 20. The breaking occurs by means of arm 21 which is linked to brake lever arm 22. This arm pivots about pin 23 and when pressure is exerted on the pressure sensing piston 19 pivoting about pin 23 causes the brake lever arm 22 to exert pressure on the spinning indicator 20 at surface 24. Preferably the displacement of the pressure sensor piston 19 is linear and is maintained as such by a four bar link mechanism in parallelogram configuration including the pressure sensor piston mounting and the brake pad support. When this braking engagement takes place, toothed belt 10 is prevented from further rotation which prevents energy from spring 6 being transmitted via pulley 17 to the door 3 until the pressure exerted by the fluid container on pressure sensing piston 19 drops. Also, at the same time the energy from spring 6 is prevented from being transmitted via pulley 17 to the door 3 via pulley assembly 15 due to the braking of shaft 25 via spinning indicator 20. The braking action on spinning indicator 20 is transmitted via shaft 25 which is linked to shaft 26 which has pulley 11 thereabout and which is also linked to the toothed belt 10. When toothed belt 10 is prevented from rotation no energy from spring 6 can be imparted via toothed belt 13 and pulley assembly 15 to the door 3.

Thus, by utilising these constant pressure device mechanisms, a constant pressure is always maintained in the fluid being administered to a patient.

Figure 3:
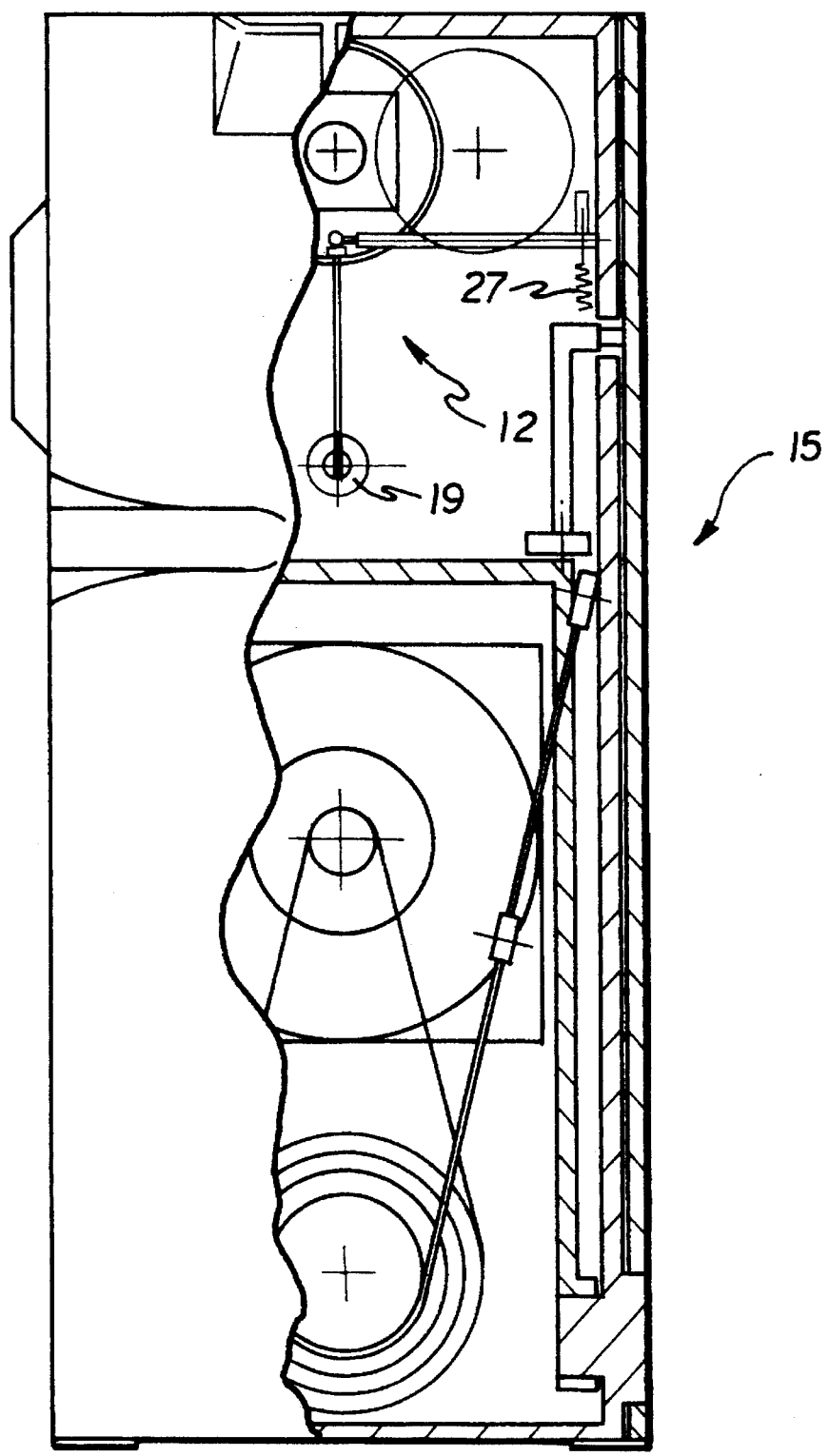
FIG. 3 shows a front elevational part sectional view of the constant flow controller showing the relationships between the pulley systems which effect energy transfer through the device according to one embodiment.

FIG. 3 shows a front view of the constant pressure device showing the braking assembly 12 and the pulley system 15. The braking system 12 is restored to a dissengaged position by means of restoration spring 27 as shown in FIG. 1. Restoration spring 27 maintains the braking assembly 12 in the dissengaged position until pressure is exerted by the administration fluid on the pressure sensor piston 19.

Figure 4:
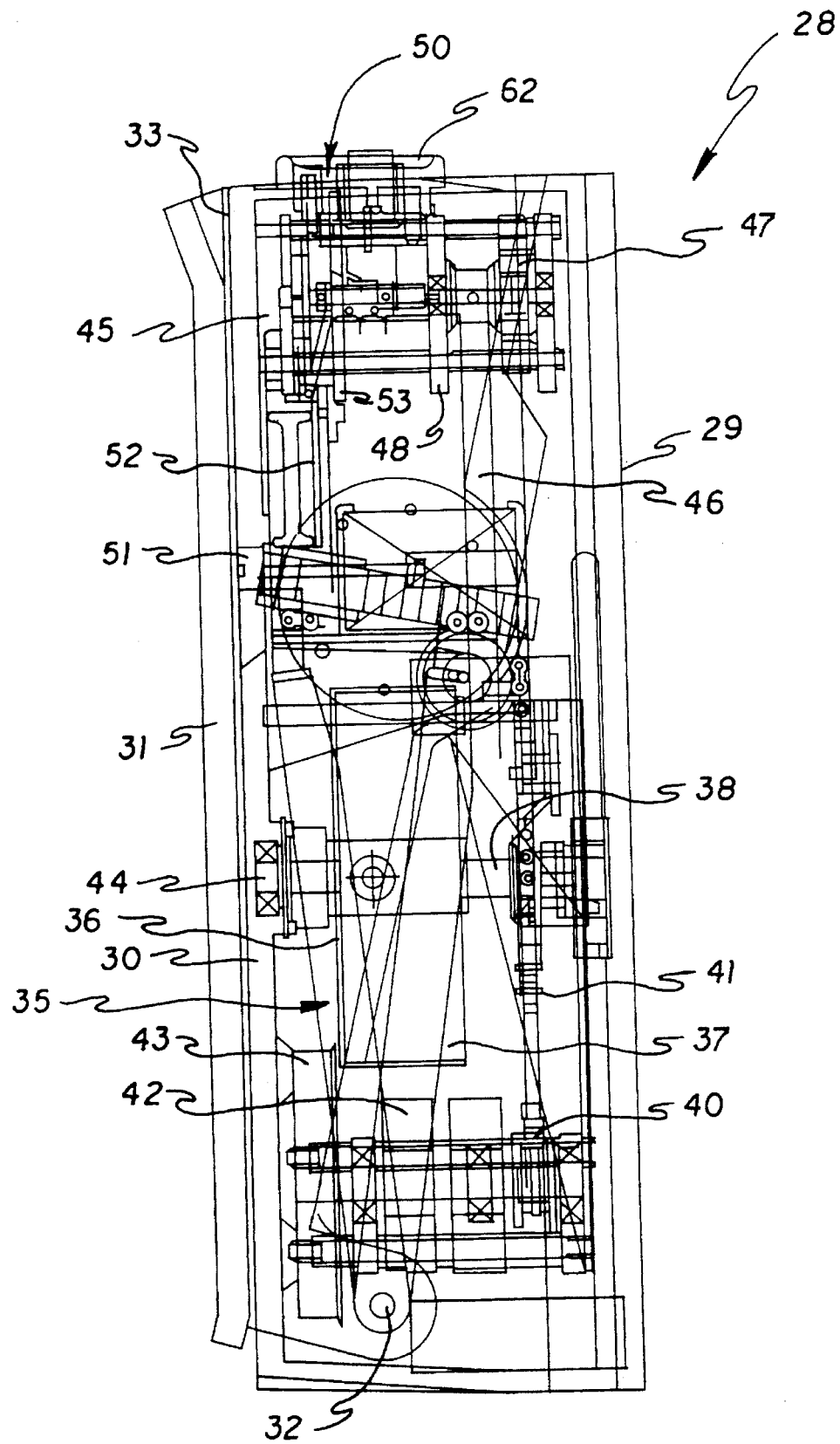
FIG. 4 shows a side elevational view of an alternative embodiment of the invention.

FIG. 4 shows a side elevational view of an alternative embodiment of a constant pressure device 28. The constant pressure device comprises outer housing 29 and an inner housing 30. Attached to the outer housing is a casing 31 which is adapted to pivot about pivot pin 32. Between the outer housing 29 and the casing 31 is a recess 33 into which recess a fluid reservoir 34 (FIG. 5) is placed. This may be in the form of a plastic bag or other material conducive to deformation under pressure.

Constant pressure device 28 comprises within the inner housing 30 an energy storage means 35 which comprises a secondary housing 36 which houses a spiral spring 37. The energy storage means also comprises an axle 38 passing through the secondary housing 36 about one end of which the spiral spring 37 is disposed. Cog wheel 40 engages with a linkage chain 41 which also engages a cog wheel 42 which is placed about a wheel 43 which is linked to the energy inducer 44. A cog wheel (not shown) which is mounted on axle 38 is linked to a gearing assembly 45 via a drive belt 46, the gearing assembly comprises gear wheels 47 and 48.

Constant pressure device 28 is also adapted with a breaking assembly 50 which is responsive to the pressure exerted on a pressure button 51 exceeding a predetermined maximum value to deactivate the drive of the device.

The pressure button 51 is linked to a lever arm 52 via a 4 bar link mechanism such that when the pressure of the fluid in the fluid reservoir 34 (FIG. 5) exceeds a predetermined maximum value the push rod 52 is urged towards disc 53 which is associated with the gearing system. This results in deactivation of the drive of the flow controller.

When the constant pressure device is to be loaded for use energy is induced into the energy storage means 35 by means of a crank arm. When energy is to be induced into the spiral spring 37 the crank arm is rotated such that the spiral spring 37 is advanced to a condition of high tension thus potential energy. Once the required amount of energy has been induced into the spiral spring 37, at the same time the casing 31 is displaced away from the outer housing 29 enabling a fluid reservoir 34 (see FIG. 5) to be placed in recess 33. When the energy is released from the energy storage means motion is imparted to linkage via the cog wheel 40.

Figure 6:
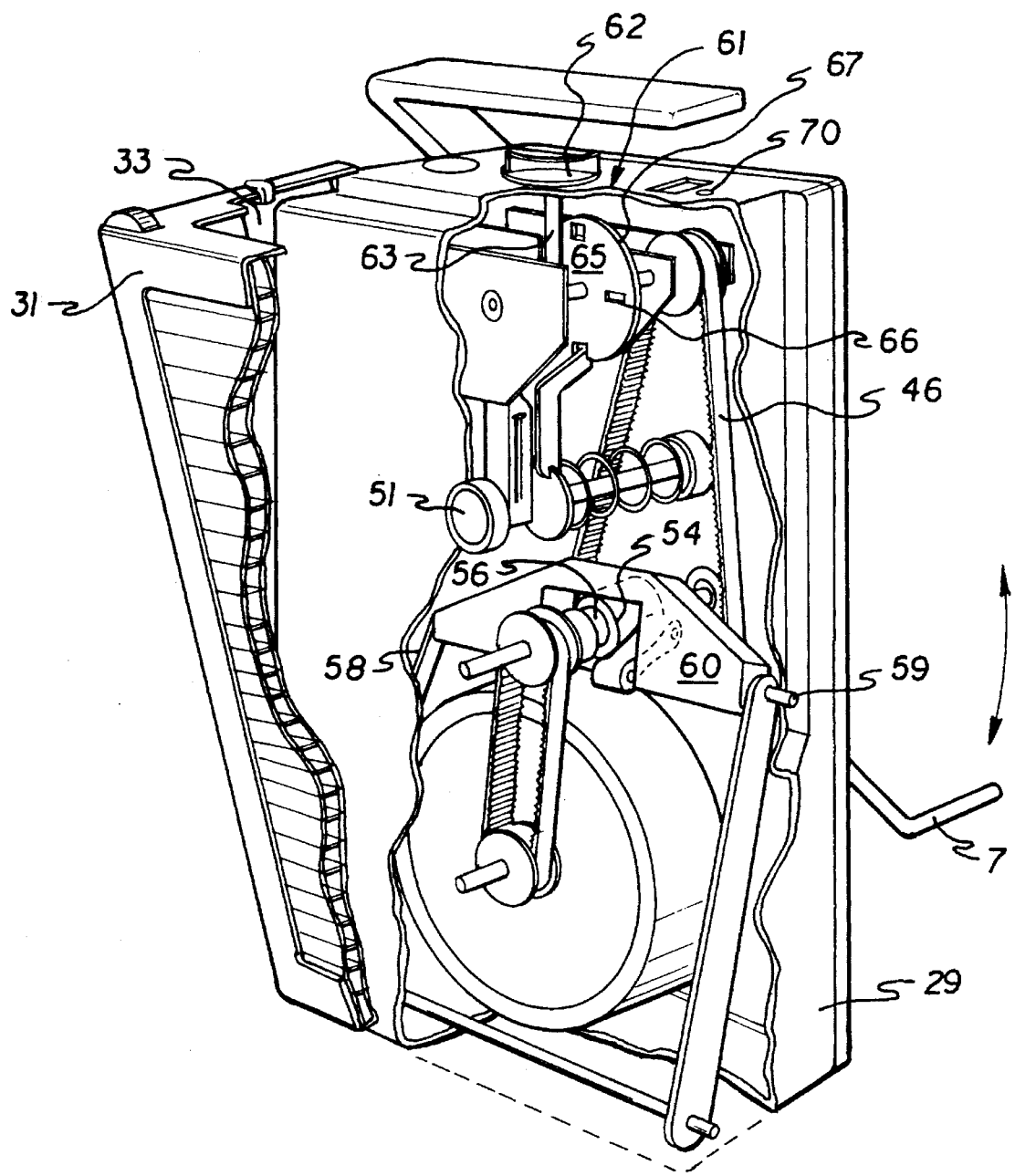
FIG. 6 shows an isometric cut away view of one embodiment of the constant pressure device.

Referring to FIG. 6, the casing 31 has recesses which receive pins 58 and 59 respectively of linkage 60. Linkage 60 is directly connected to the drive nut case 54. This has the effect that the casing 31 moves in response to movement of the drive nut case along the drive thread 56 when energy is being induced or released from the energy storage means. Thus, when the energy storage means is at a condition of maximum energy storage, the casing 31 is rotated away from the outer housing 29 to its maximum rotational position. When the fluid reservoir 34 is inserted in the recess 33, by virtue of the interengagement between the recesses and pins 58 and 59 respectively, the casing 31 is urged towards the outer housing 29 thereby exerting pressure on the fluid reservoir. The pressure is exerted at a constant rate. However, if the pressure exceeds a predetermined maximum value, the pressure button 51 absorbs this pressure and deactivates the drive by operation of push rod 52. When the pressure falls below the threshold value the drive recommences. When the fluid is discharged fully from the fluid reservoir 34 the casing 31 exerts pressure on the pressure button 51.

As shown in FIG. 6, the constant pressure device 28 also has a control assembly 61 which enables an operator to stop, test, run or advance the mechanism of the flow controller. This works by turning knob 62 which is connected to a spindle 63 which in turn has an engagement disc (not shown) which engages selectively with rotating disc 65 via lugs 66.

A further rotating disc 67 which is directly coupled to gearing assembly via a shaft is located in very close proximity to rotating disc 65 and such that the space between the two rotating discs can be filled with a viscous oil. When engagement disc engages with the lugs 66 of rotating disc 65 which thereby is held stationary, the speed of the rotating disc 67 is controlled by the viscous oil and the drive speed is caused to operate at its normal rate via the gearing assembly 45 and drive belt 46. When an engagement disc disengages from lugs 66 of disc 65 it is allowed to rotate and the drive is able to operate at a higher speed to allow rapid adjustment for variations in size of fluid reservoir 34. This higher speed is limited by a centrifugal speed governor attached to rotating disc 65. The outer housing 29 of the constant pressure device 28 is adapted with a carry handle 7 for portability.

Preferably the constant pressure device according to this present embodiment accommodates either a 500 or 1000 ml infusion bag and can dispense a predetermined fraction of either sized bag. The constant pressure device also has an audio visual alarm 70 indicating infusion limit reached. The constant pressure device can either by used as a portable device or can be clamped to a support.

As the constant pressure device operates independently of gravity it can operate at any angle or height and is therefore fully portable. It is most useful for paramedics in ambulances and helicopters as well as in hospitals and as a preferred option to gravity drip systems.

The flow of the constant pressure device is continuous and preferrably operates at or around a pressure of 30 KPa to 60 KPa plus or minus 5 KPa.

Figure 5:
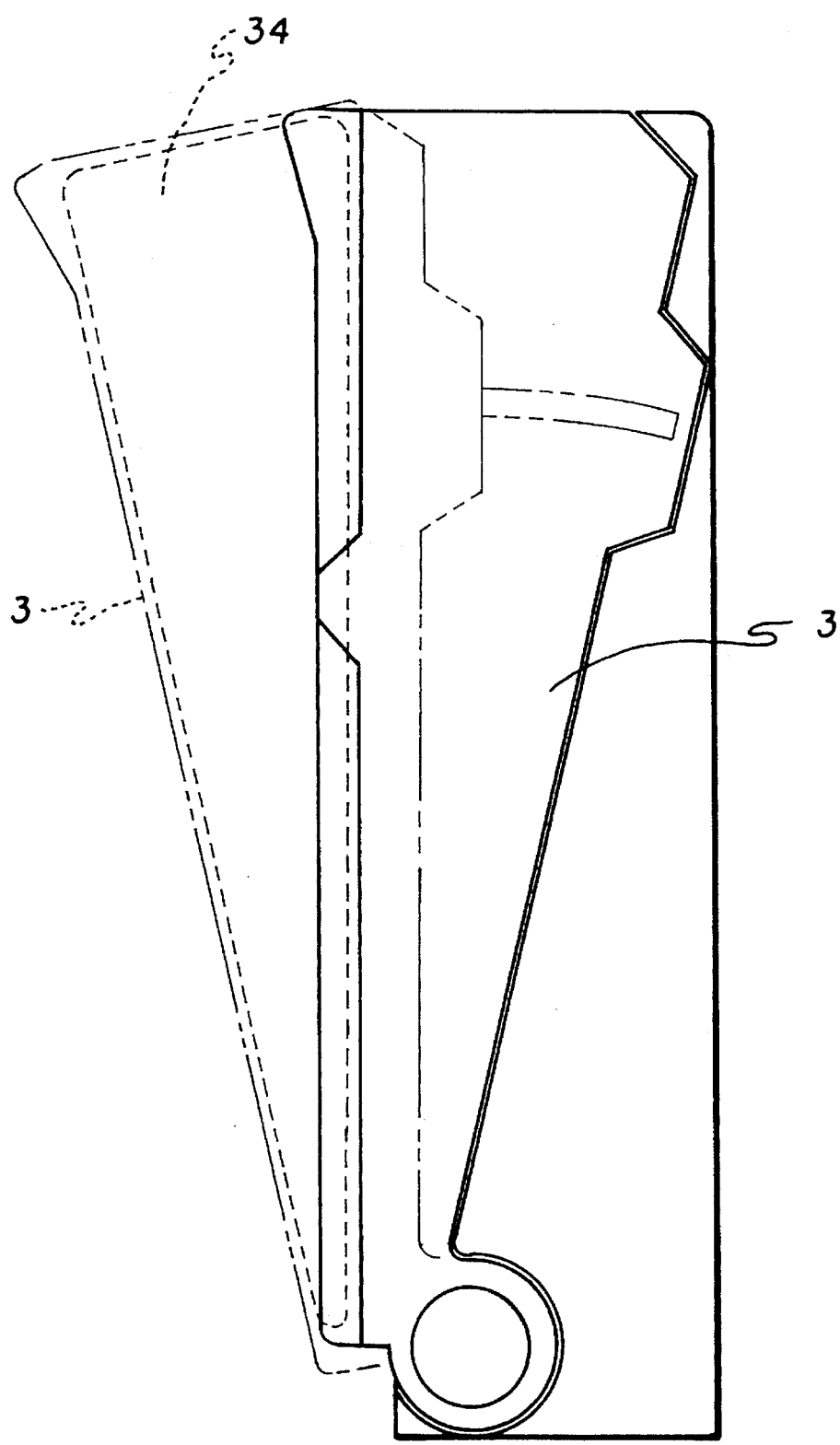
FIG. 5 shows a side external elevational view of the constant pressure device showing the pressure exerting door in the closed or equilibrium position and in the open position.

FIG. 5 shows a side elevational view of the housing of the constant pressure device showing the full configuration of the casing in both the opened and closed positions.

Figure 7:
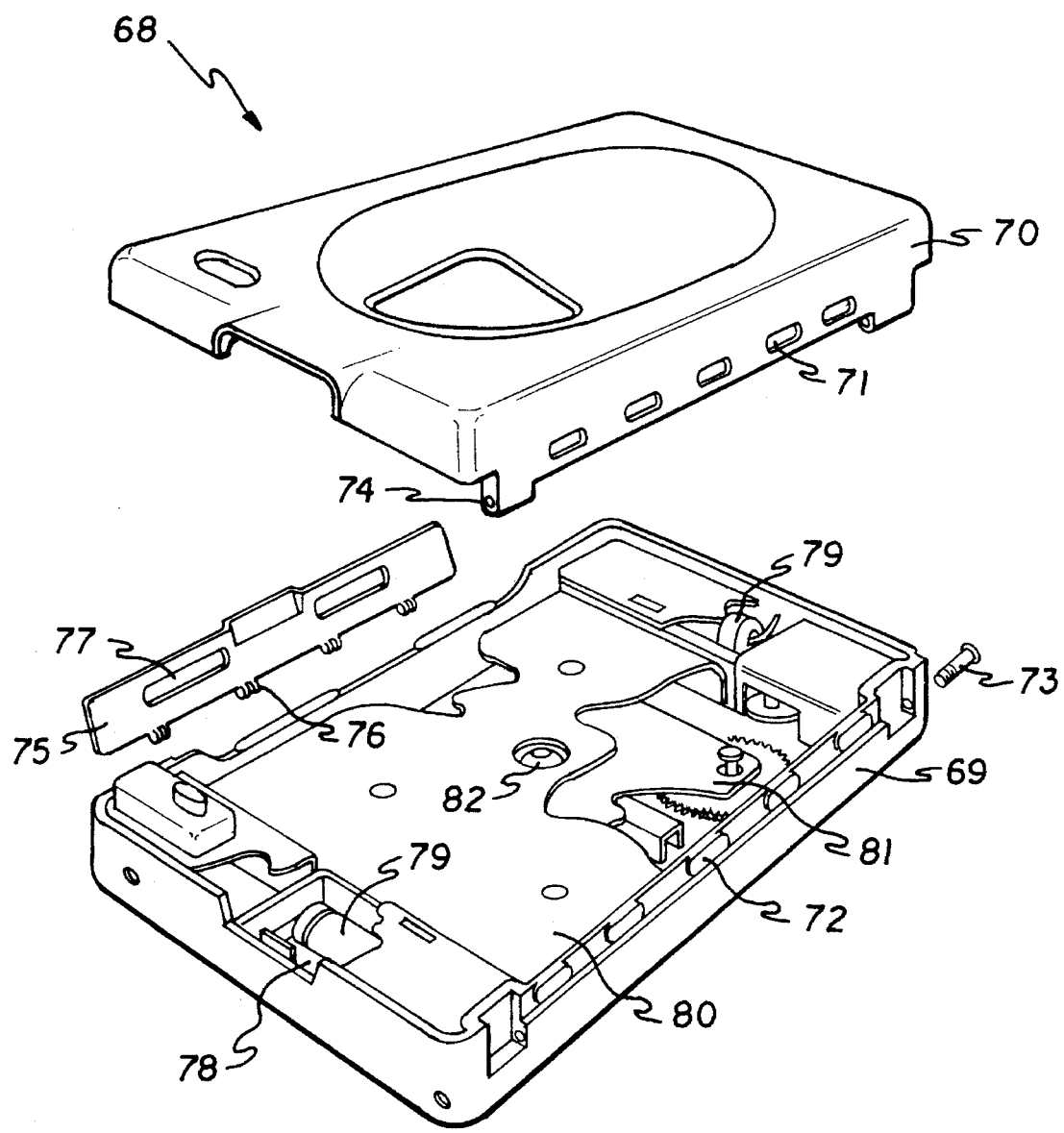
FIG. 7 shows an alternative embodiment of the present invention.

FIG. 7 shows an alternative embodiment of the constant pressure device suitable for infusion bags/reservoirs typically from 50 ml to 250 ml.

Referring to FIG. 7 there is shown an exploded isometric view of the constant pressure device 68 according to an alternative embodiment of the present invention. The device comprises a housing 69 which is adapted for coupling with a casing 70. The casing 70 is adapted with openings 71 which when it engages with the housing 69 engage protrusions 72. The protrusions 72 and openings 71 are optional. In the alternative a simple catch (not shown) is used where the constant pressure device operates at low pressures for instance within the range 15 KPa to 25 KPa. The pivotal linkage between the casing 70 and the housing 69 is effected by means of pin 73 engaging openings 74 in the casing. In an alternative embodiment (not shown) the opening 74 may travel the full length of the casing so that a pin acting in the same manner as pin 73 may pass through the opening to provide a pivotal linkage. When the casing is anchored to the housing 69 in order to close the casing down on the housing pivoting catch 75 which is anchored to the housing 69 by means of anchorages 76 rotates towards the housing and engages protrusions on the casing (not shown) via holes 77.

The housing hinge has been designed to carry half the squeezing force (450N) with a minimum of coring for hinge pins. As the casing closes, a series of lugs engage in holes in the casing edge, allowing the high forces to bypass the hinge pins.

The casing latch may use a buckle arrangement and in a similar way requires strong lugs on the housing. The buckle is hinged onto the housing but with a different arrangement to that of the casing. Since the joint needs only a limited movement, and also needs a self-closing action, it is done with little tabs on the buckle projecting through slots in the housing. A simple spring wire on the inside of the housing provides a self closing action by pushing on the tabs.

The casing and housing may be designed to facilitate the use of high flexural strength plastics.

Side cores may be used for creating the holes on the hinge side according to the first embodiment. A polycarbonate window can be placed in a recessed opening from the pressure side. Radiused flanges are provided around the edges to increase the stiffness.

In one embodiment the casing 70 is locked into position on the housing 69 by means of a wire linked to casing 70 which is adapted to rotate towards the casing and engage a ledge on the casing 70 causing a clamping force to induce a tight interfitting between the casing 70 and the housing 69. The housing 69 also comprises a receptacle 78 for housing an energy source which is provided according to a preferred embodiment by means of a non-chargeable or chargeable dry cell battery 79. In use, when a fluid is to be discharged at a constant rate from a reservoir, the reservoir (not shown) is placed on pressure plate 80 which is directly or indirectly linked to a drive mechanism which is powered by the battery 79 and an intermediate electric motor therebetween. When the reservoir is placed on presure plate 80 the casing 70 is closed such that the fluid reservoir is sandwiched between the plate 80 and the casing 70. When the device is turned on, power to the electric motor drives a series of gear wheels which are linked to pressure plate 80. The power induces movement in the pressure plate 80 until such time as the operating pressure is reached. At this moment the pressure is sufficient to actuate a power isolation switch 82 which is preset to operate at or slightly above the operating pressure. When the pressure falls below the operating range, the switch reactivates the drive in order to induce more pressure in the pressure plate 80. By this means fluids from the reservoir can be delivered at a constant pressure independently of gravity facilitating a constant flow rate to the patient with appropriate flow rate control device and is therefore portable. Thus, as the reservoir empties the device is constantly adjusting by actuation or deactuation such that the operating pressure is always maintained within tolerable limits.

Figure 8:
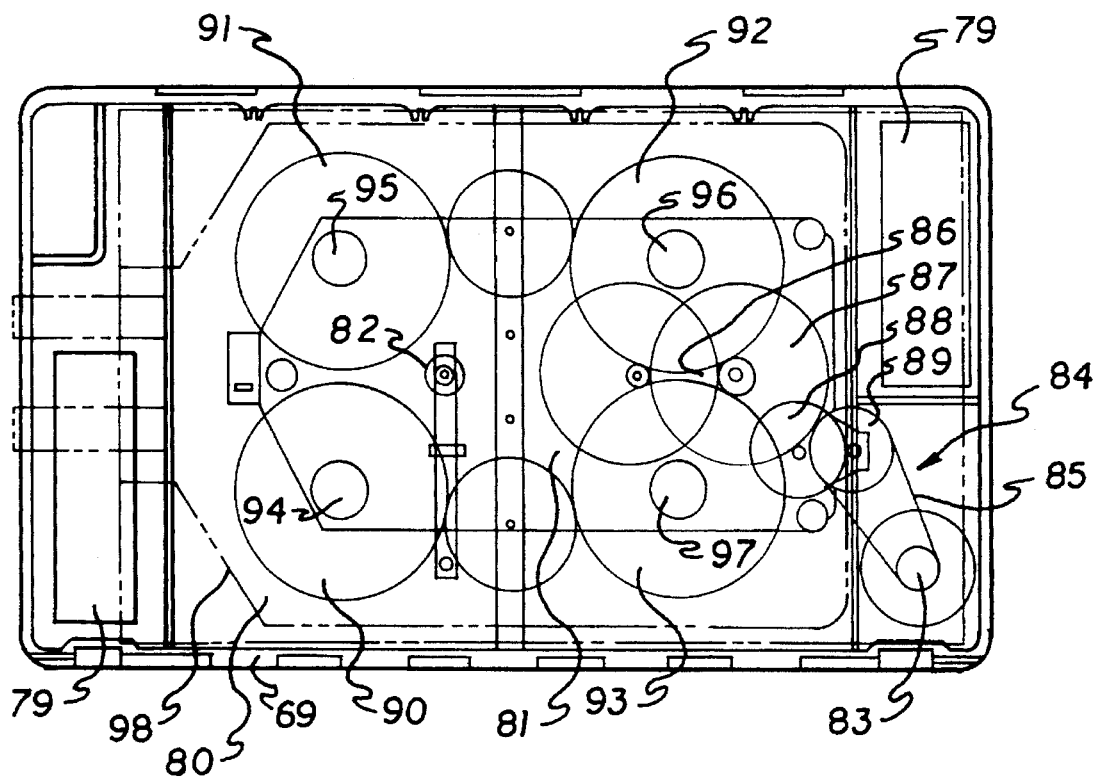
FIG. 8 shows a plan view of internal components of the constant pressure device shown in FIG. 7.

Referring to FIG. 8 there is shown a plan and cross sectional view of the internal workings of the device according to the embodiment shown in FIG. 7.

Power from the preferably two dry cell batteries 79 actuate electric motor 83. The motor 83 is linked to gear assembly 84 by means of a drive belt 85. The drive of the motor is geared down via the gearing assembly 84 by means of 4 gears and pinions 86, 87, 88 and 89. The gearing assembly 84 is linked to gear wheels 90, 91, 92 and 93. Each of these gear wheels have respectively at their base a thrust race to transmit axial loading to housing 69 and within them a female thread through which thrust screws 94, 95, 96 and 97 are mounted and are capable of axial movement. The assembly is held in position by means of a drive assembly plate 81 over which is superimposed pressure plate 80. FIG. 8 shows the outline of a reservoir containing fluid 98 disposed within the housing 69.

When the constant pressure device is turned on, the motor drives the respective gears such that the pressure plate 80 is elevated inducing pressure in the fluid contained in the reservoir 98 with the assistance of the casing 70. When the predetermined operating pressure has been reached pressure switch 82 operates to deactivate drive by the electric motor by disconnecting the energy source. The pressure sensing switch preferably comprises a button support on a cantilevered wire spring or strip. The reservoir pushes the button down to break the electrical contact. Initial tests indicate that gold plated contacts without click action are suitable. The components are mounted directly into the rear face of the pusher plate. As fluid level drops the pressure reduces and once it has fallen beneath the predetermined operating flow rate range the motor will reactuate to move the pressure plate 80 further towards the casing so that the fluid in the reservoir returns to the operating pressure.

Figure 9:
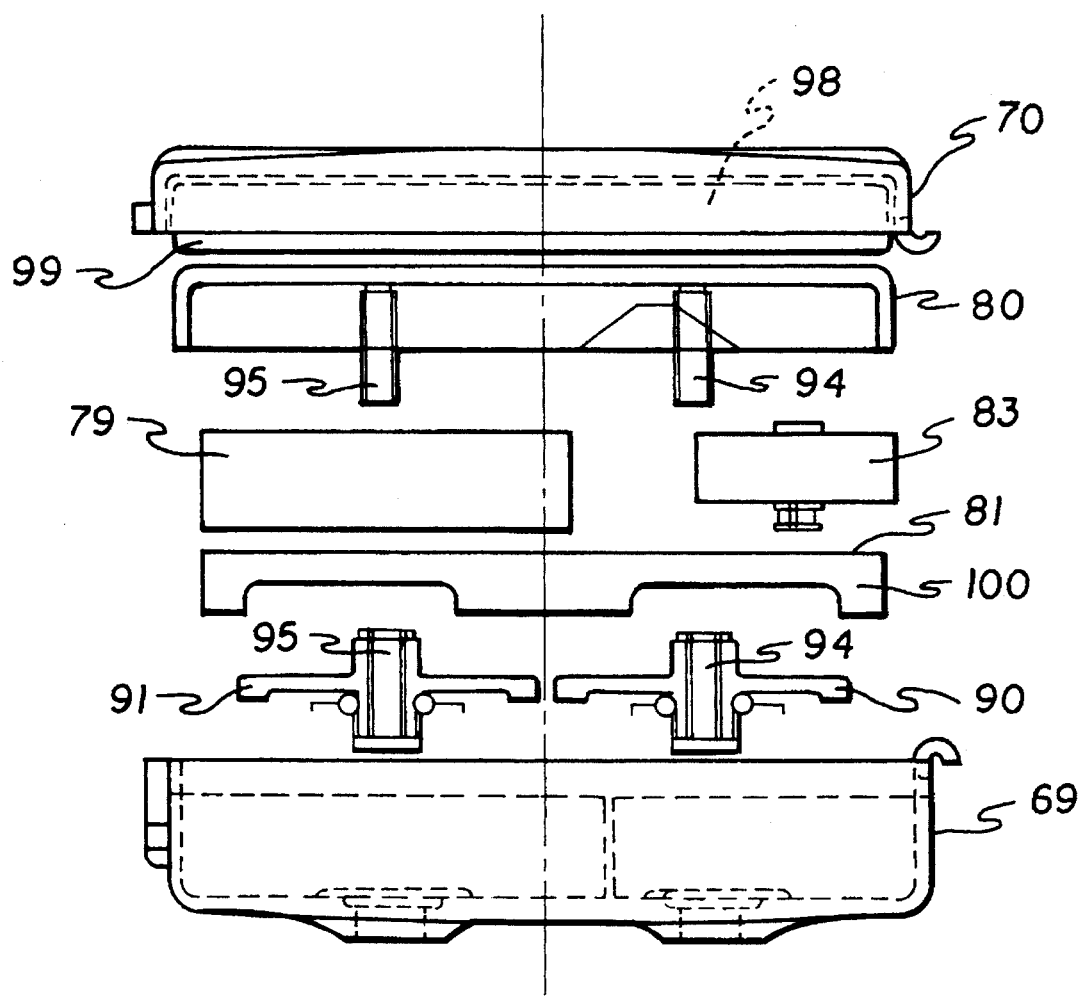
FIG. 9 shows an exploded end view of the device in FIG. 8.

FIG. 9 shows an exploded elevational view of the various component parts of the constant pressure device. FIG. 9 shows the casing 70 superimposed over the pressure plate 80. The reservoir 98 is placed in intersticies 99. Also shown is battery 79 and motor 83 along with drive assembly plate 81. Gear wheels 90 and 91 are shown with thrust screws 94 and 95 respectively. Upon rotation of the drive wheels 90 and 91 as the thrust screws 94 and 95 are fixedly attached to pressure plate 80 rotation in one direction of gear wheels 90 and 91 causes elevation of the thrust screws 94 and 95 and consequent elevation of the pressure plate 80 which induces pressure against the fluid reservoir. Similarly with gear wheels 92 and 93 corresponding thrust screws 96 and 97 elevate to cause axial movement in pressure plate 80 such that the movement is evenly distributed over the full area of the pressure plate 80.

Tests have shown that the thrust screws can optionally be telescopic to increase the length of the stroke of the pressure plate or reduce the depth of the device for the same stroke.

An ON/OFF switch (not shown) positioned externally on housing 69 is so arranged that when switch is in the off position the electric motor 83 is automatically caused to operate in a reverse direction and gear wheels 90, 91, 92 and 93 similarly rotate in the reverse direction. Thrust screws 94, 95, 96 and 97 being fixedly attached to the pressure plate 80 draw the pressure plate down to its lowest initial start position. On reaching that position the pressure plate activates a contact switch (not shown) fixed to drive assembly plate 81 which automatically isolates the energy source 79 from the electric motor 83 and no further actuation occurs. Further use of the constant pressure device requires switch to be in ON position which allows energy to bypass the contact switch and cause the motor to travel in a forward direction and elevate pressure plate 80 as previously described.

Preferably the drive assembly plate 81 is 0.75 mm thick steel and is located immediately just under the pressure plate 80 when the pressure plate is in its fully home or start position.

The drive assembly plate 81 is fixed by screws to bosses at any convenient location on the internal walls of housing 69. A function of the assembly plate is to hold one end of the shafts about which the gears rotate. The opposite end of the gear shafts are held in position by recesses within bosses located on the base of housing 69.

Another important function of the pressure plate is to retain gear wheels 90, 91, 92 and 93 when axial forces are placed on them by the thrust screws and thereby preventing the ball thrust bearings from opening.

The drive assembly plate also has a dished portion to clear the pressure sensing switch when the pressure plate is fully home.

FIG. 9 further shows a cross member 100 which is fixed at its centre by two screws passing through bosses in the base of housing 69 and pass through the cross member to attach to drive assembly plate 81 and thereby providing one means of fixing it to the housing. Cross member 100 is thereby tightly sandwiched between the gear assembly plate and the housing base to reduce deflection of the housing base during normal operation by transferring the force at the centre of the housing base to the edges of the housing base via the cross member.

At one point the drive assembly plate protrudes through a gap in the flange of the pressure plate to carry the axle for the first stage of reduction gearing.

It will be recognised by persons skilled in the art that numerous variations and modifications of the constant pressure device such as but not limited to using the constant pressure device in prior art and novel administration sets either with or without additional flow control or fluid flow valves can be made without departing from the overall spirit and scope of the invention as broadly described herein. It is further to be understood that the present invention encompasses any and all embodiments within the scope of the following claims.

I claim:

1. A pressure control device for use with a flexible walled fluid carrying container, the device being adapted to control the pressure of fluid in the container within a predetermined pressure range whether the fluid is being discharged from the container or not, the pressure control device being suitable for use with a fluid flow controller which controls the flow rate of fluid being discharged from the container, the pressure control device including:

a housing having a chamber therein for receiving the fluid carrying container;

pressure generating means which is movable so as to apply a force on the fluid carrying container for generating pressure in the fluid within the container;

drive means operatively connected to a power source so as to be able to adopt either an activated condition or a deactivated condition, said drive means operatively connected to said pressure generating means so that when in the activated condition it causes movement of said pressure generating means to apply a force on said container and in the deactivated condition, movement of the pressure generating means ceases;

pressure monitoring means for monitoring the pressure of the fluid within said container, the monitoring means including sensor means which is adapted to engage the wall of the container; and control means which is responsive to said monitoring means and operable to cause said drive means to adopt either the activated condition or the deactivated condition, the arrangement being such that in operation the drive means is being activated or deactivated so that the pressure of the fluid within the container is maintained within the predetermined pressure range.

2. A device according to claim 1 wherein said housing comprises a body and a cover with the chamber therebetween, said cover being movable and being operatively connected to said drive means such that the cover moves when said drive means is in the activated condition.

3. A device according to claim 1 wherein said pressure generating means includes a pressure plate responsive to actuation of said drive means.

4. A device according to claim 3 wherein said drive means comprises an electric motor which is linked to a gearing assembly which is in turn linked to drive wheels operatively connected to said pressure plate.

5. A device according to claim 4 wherein each said drive wheel has associated therewith thrust screws which travel normally to the plane of rotation of said drive wheels.

6. A device according to claim 5 wherein said thrust screws are attached to said pressure plate such that the movement of said pressure plate is dependent upon movement of said thrust screws.

7. A device according to claim 6 wherein said thrust screws are directly attached to said pressure plate.

8. A device according to claim 5 wherein said sensor means includes a pressure switch, which operates to isolate said motor from the power source prohibiting movement of said pressure plate when the fluid pressure exceeds the predetermined operating range.

9. A device according to claim 8 wherein said drive means is actuated and deactuated in response to the fluid pressure falling below or exceeding the predetermined operating range.

10. A device according to claim 9 wherein said electric motor is linked to a gearing assembly via a drive belt, said gearing assembly imparting drive to a series of drive wheels which are indirectly linked to the pressure plate via said thrust screws.

11. A device according to claim 10 wherein, when said drive wheels are rotated so that each of said thrust screws are advanced in a direction along the axis of said drive wheels to urge said pressure plate towards the fluid reservoir.

12. A device according to claim 11 further comprising a microprocessor linked to an alarm to signal a reduced power condition or a pressure switch failure condition.

13. A device according to claim 12 wherein said thrust screws evenly distribute pressure on said pressure plate.

14. A device according to claim 2 wherein said housing and said cover are substantially rectangular.

15. A device according to claim 14 wherein stored energy is provided by at least one dry cell battery.

16. A device according to claim 15 wherein said dry cell battery is chargeable.

17. A device according to claim 15 wherein said dry cell battery is non-chargeable.

18. A device according to claim 15 further comprising means to selectively stop, test, fast advance or permit drive of the drive means via transmission means.

* * * * *